(12) United States Patent
Boezaart et al.

(10) Patent No.: US 10,292,858 B2
(45) Date of Patent: May 21, 2019

(54) IMMOBILIZATION DEVICE UTILIZING A SPLINT AND PILLOW COMBINATION

(71) Applicants: Theodoor Christian Boezaart, Blacksburg, VA (US); Andre Boezaart, Gainesville, FL (US)

(72) Inventors: Theodoor Christian Boezaart, Blacksburg, VA (US); Andre Boezaart, Gainesville, FL (US)

(73) Assignee: TSWELOPELE LABS, INC., Richmond, VA (US)

( * ) Notice: Subject to any disclaimer, the term of this patent is extended or adjusted under 35 U.S.C. 154(b) by 467 days.

(21) Appl. No.: 14/951,926

(22) Filed: Nov. 25, 2015

(65) Prior Publication Data

US 2016/0184126 A1    Jun. 30, 2016

Related U.S. Application Data

(60) Provisional application No. 62/084,436, filed on Nov. 25, 2014.

(51) Int. Cl.
*A61F 5/058* (2006.01)

(52) U.S. Cl.
CPC .......... *A61F 5/05816* (2013.01); *A61F 5/058* (2013.01); *A61F 5/0585* (2013.01); *A61F 5/05841* (2013.01)

(58) Field of Classification Search
CPC ............ A61F 2005/0167; A61F 5/0102; A61F 2005/0139; A61F 5/0125; A61F 5/058; A61F 5/0123; A61F 5/0585; A61F 5/05841; A61F 5/05816
See application file for complete search history.

(56) References Cited

U.S. PATENT DOCUMENTS

| | | | |
|---|---|---|---|
| 8,216,165 B2 * | 7/2012 | Ravikumar | A61F 5/012 602/13 |
| 8,858,478 B2 * | 10/2014 | Purdy | A61F 5/0111 128/DIG. 20 |
| 2014/0107547 A1 * | 4/2014 | Drey | A61H 9/005 601/151 |

* cited by examiner

*Primary Examiner* — Ophelia A Hawthorne
(74) *Attorney, Agent, or Firm* — Bechen PLLC

(57) ABSTRACT

The present invention provides a combination of a splint and a pillow for use in treating and immobilizing a patient. The combination includes a first portion encased in an airtight container and a second portion also encased in an airtight container. The first portion and the second portion are interconnected by an air flow valve having a air flow regulator for controlling airflow between the portions. The first portion may include bean-bag or similar splint and the second portion includes a foam component. The two portions share the same air such that when the first portion is inflated, the second portion is deflated. Wherein, upon opening of the airflow regulator, the air pressure passes between the first portion, deflating the first portion, into the second portion, thus inflating the second portion.

20 Claims, 3 Drawing Sheets

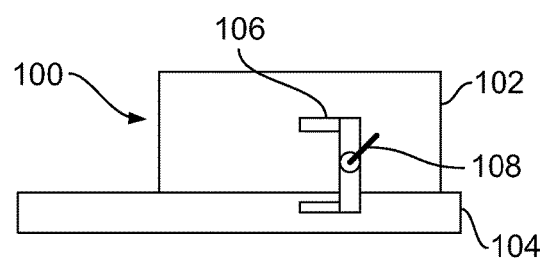
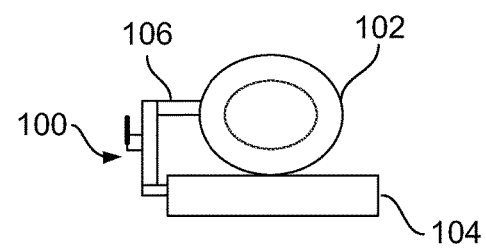
FIG. 1  FIG. 1A
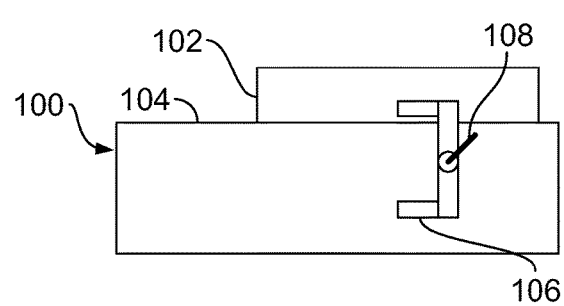
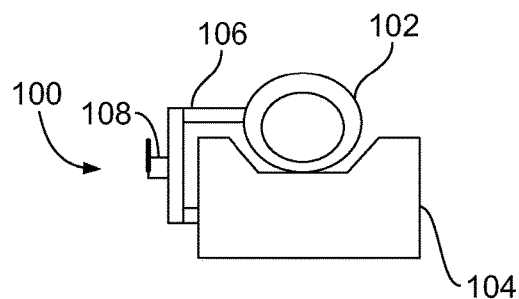
FIG. 2A  FIG. 2B
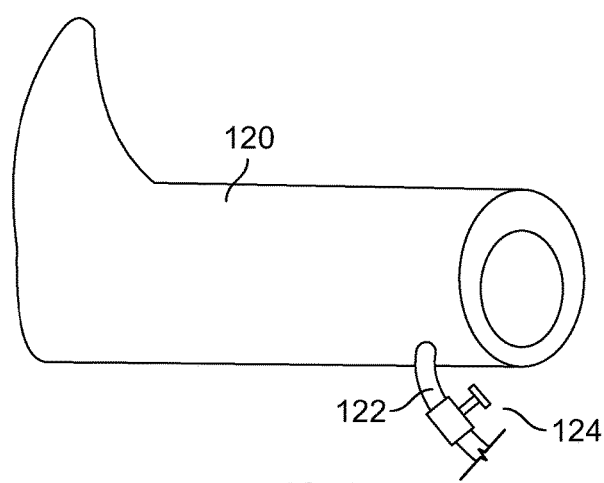
FIG. 3

IMMOBILIZATION DEVICE UTILIZING A SPLINT AND PILLOW COMBINATION

RELATED APPLICATIONS

The present invention relates to and claims priority to U.S. Provisional Patent Application Ser. No. 62/084,436 entitled "IMMOBILIZATION DEVICE UTILIZING A SPLINT AND PILLOW COMBINATION" filed Nov. 25, 2014

COPYRIGHT

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD OF THE INVENTION

The invention relates generally to medical devices used for immobilization of a patient's limb, and more specifically to the utilization of a splint and a pillow in combination with air pressure adjustments of the combined elements for improving patient safety and comfort.

BACKGROUND OF THE INVENTION

When a patient needs to be immobilized, there are numerous techniques currently available. For example, if a patient has a broken leg, the leg can be splinted without applying pressure to the leg, or impeding blood supply or blood flow to the limb or otherwise creating pressure points. One technique for applying a splint is the use of an air cast applied around the limb, the inflation of the air encapsulates the limb and thus provides security from unwanted movement.

While not readily used in the immobilization of a limb in a triage scenario, another immobilization technique is the use of a bean-bag device. The concept of the bean-bag has been used for positioning of patients on operating room tables for surgery, for example positioning patients for neurological cranial remodeling surgery.

In addition to immobilization, another technique for insuring patient safety is to elevate the limb. This may commonly be done using a pillow, having the limb rest upon the pillow. The pillow includes a combination of rigidity to support the limb, but also a degree of cushion to minimize any jarring of the limb.

Problems can arise in the elevation of the limb to be placed in the foam or soft material. Patients can experience additional discomfort while getting the limb into an elevated position.

Thus, while it important to immobilize a limb and elevate the limb, it is also important to perform such actions with maximum immobilization and minimum disruption or discomfort to the patient. The techniques for elevating limbs and securing limbs in a splint or other ambulatory methods are disparate techniques not previously.

There are no known techniques for combining the beneficial rigidity of bean-bag technology with foam elevation techniques. As such, there exists a need for the combined technologies improving patient immobilization.

BRIEF SUMMARY OF THE INVENTION

The present invention provides a combination of a splint and a pillow for use in treating and immobilizing a patient. The combination includes a first portion encased in an airtight container and a second portion encased in a separate airtight container. The first portion and the second portion are interconnected by an airflow valve having an air flow regulator for controlling airflow between the portions.

In one embodiment, the first portion includes an air-cast, a bean-bag or similar splint material and the second portion includes a foam component. The two portions share the same air such that when the first portion is inflated, the second portion is deflated. Wherein, upon opening of the airflow regulator, the air pressure passes from the first portion, deflating the first portion, and inflating the second portion.

The combination system allows for the splinting of a limb by placement of the limb in the first portion, the first portion being inflated. The inflated first portion creates a generally soft encasement and immobilization of the limb as the inflation of the first portion allows for freer movement of the beads within. As the first portion is originally inflated, the second portion is originally deflated, thus a foam material is flattened, capable of being readily slid under the limb with minimal patient disruption. The patient's limb can then be secured within the first portion and on top of the second portion.

Upon engagement of the airflow regulator, the first portion deflates, such that the beads become more tightly engaged forming a more solid encasement and immobilization around the limb. Concurrently, as the first portion deflates, the second portion inflates, elevating the limb and allowing the foam material to expand into a memory position. Upon adjustment of the airflow, the first portion becomes a solid splint and the second portion becomes a foam pillow elevating the limb.

The combination includes additional embodiments as described in further detail below.

BRIEF DESCRIPTION OF THE DRAWINGS

A better understanding of the disclosed technology will be obtained from the following detailed description of the preferred embodiments taken in conjunction with the drawings and the attached claims.

FIGS. 1-1A illustrate a side view and a front view of a first embodiment of the combination;

FIGS. 2A-2B illustrate a side view and a front view of a second embodiment of the combination;

FIG. 3 illustrates a perspective view of one embodiment of the first element providing a splint;

DETAILED DESCRIPTION

Figure 4:
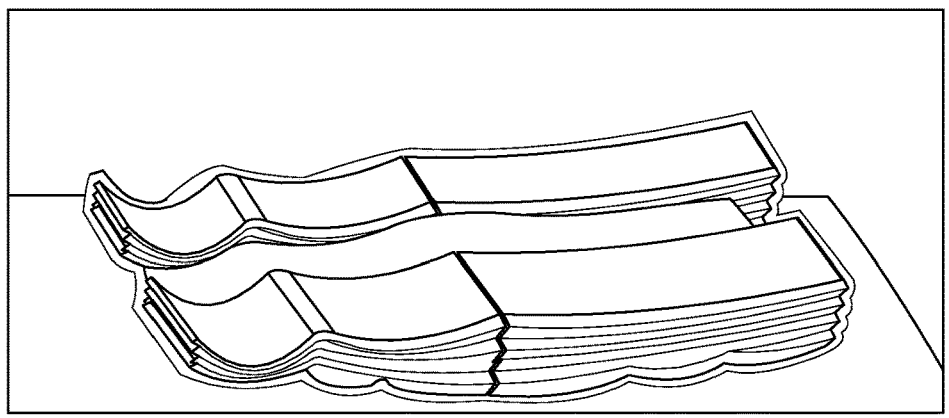
FIG. 4 illustrates a representation of one embodiment of the second element in a compressed or deflated state.

Various embodiments are described herein, both directly and inherently. However, it is understood that the described embodiments and examples are not expressly limiting in nature, instead illustrate examples of the advantageous uses of the innovative teachings herein. In general, statements made in the specification of the present application do not necessarily limit any of the various claimed inventions and it is recognized that additional embodiments and variations recognized by one or more skilled in the art are incorporated herein.

FIG. 1 illustrates a side view of the combination 100 of a first portion 102 and a second portion 104. The first portion 102 and the second portion 104 are connected via an air tube 106 have a stop valve 108 therebetween.

Similarly, FIG. 1a illustrates a front view of the combination 100 including the first portion 102 and the second portion 104, with air tube 106 and valve 108.

In one embodiment, the first portion 102 operates as a splint via using spherical material, such as a beanbag. A beanbag for medical use can basically be described as a sealed airtight bag containing thousands of beads that are typically round and of variable sizes. In one embodiment, the beads may be tiny plastic (typically polystyrene) beads. The beanbag is normally soft (when inflated to ambient pressure—or not deflated) but when the air is withdrawn through suction, a vacuum below ambient pressure is created inside the beanbag, which forces the plastic beads together. As a consequence, the beanbag becomes hard and molds itself precisely around the patient's body or body parts without exerting any pressure on the body part holding the body part in precisely the position it was in before the air was extracted. It thus forms a molded cast that stabilizes the patient, limb or body part and keeps the patient or the body part in a stable and secure position. Pressure points are avoided as the beanbag molds itself around these pressure points and the patient's weight is distributed equally and evenly everywhere. Upon release of the negative pressure (suction) the beanbag re-assumes its original soft and unmolded shape.

The second portion 104, in this embodiment, is composed of a foam material. In one embodiment, the foam is a memory foam component, encapsulated in an air tight membrane. The foam material of a pillow is shaped in a desired form, for example, to place under a lower leg to elevate the leg as one example. This shaped material is compressible, and the foam (typically) has a "memory" so that upon release of the compression negative pressure), it returns exactly to its prior form. In one embodiment, the foam material of the pillow is covered with a soft, durable, lightweight airtight and washable material.

Visible in FIGS. 1 and 1a, the first portion 102 is connected to the second portion 104 via the air tube 106 connected to the covering membranes of the portions 102, 104. The air tube 106 includes the air flow valve 108 to regulate the flow of air, and subsequent air pressure, between the two portions 102, 104. In one embodiment, the cover has a one-way valve connector to which a negative pressure can be applied to completely compress the pillow and its foam material.

In the embodiment of FIGS. 1 and 1a, the first portion 102 is inflated and the second portion 104 is deflated. This is more readily visible relative to the illustration of FIGS. 2a and 2b described below.

In FIGS. 1 and 1a, the first portion 102 having beanbag material or similar composition is soft and pliable. The inflation of the outer layer of the first portion 102 allows for the filling elements, in this embodiment being beanbag material or similar composition, to more freely move within the air-tight casing. This free movement of the material then allows the first portion to be wrapped around the limb and secured using securing means, such as by way of example adhesive straps, or other securing means recognized by one skilled in the art. Thus the splint does not place any undue pressure on the limb.

The second portion 104, being a foam material and under pressure in a deflated for the compresses of the foam. The second portion 104 is thus a reduced size, capable of being more easily positioned under the limb having been placed in the splint, first portion 102.

It is recognized that in one embodiment, the air tube 106 may continuously connect the first portion 102 and the second portion 104. In this embodiment, the combination 100 is then transported as a single cohesive unit, wherein the splint 102 is attached to the person while the compressed foam 104 is engaged under the limb.

It is further recognized that based on safety concerns of not wanting to move an injured limb or the person in general, the first portion 102 and the second portion 104 may be separate components, with engagement means to connect to the air tube 106. For example, the air tube 106 may be directly connected to the first portion 102 with the first portion having an excess amount of air pressure, e.g. extra air contained therein, and the valve 108 in the off position. When the splint 102 is applied to the person, the splint 102 includes the valve 106 and a bottom end of the tube 106 can then be fittingly attached to second portion 104. Thus, when attached, the release of the valve 108 allows for the excess air pressure in the splint 102 to inflate the second portion 104.

It is recognized that the above example is not limiting in nature, such that the system 100 may include the tube 106 fixed to the second portion 104 and then connected to the first portion 102. In another embodiment, the first portion and the second portion may be placed in position about the person than then connected via the tube 106.

In one embodiment, an air pump may be utilized to inflate the first portion before are after engagement of the limb. An exemplary air pump can be a manual air pump or an electric air pump. Based on the degree or severity of the injury, the first portion may be engaged around the limb in a deflated or inflated position, such as for example determined by the ability to move the limb. For a severe injury, the first portion may need to be deflated to be slid under the limb, then partially or fully inflated as it is secured. Once secured, if not fully inflated yet, it can then be fully inflated to provide requisite air pressure to subsequently inflate the second portion upon opening of the air valve.

Wherein, if the portions 102 and 104 are used without beginning engagement with the air tube, one embodiment may include an additional air flow valve disposed in the portion 102/104 itself to insure keeping the portion in its original inflation/deflation state prior to engaging the air tube.

In contrast to FIGS. 1 and 1a, FIGS. 2a and 2b illustrate the combination 100 with the first portion 102 in a deflated state and the second portion 104 in an inflated state. In the embodiment of FIGS. 2a and 2b, the person would have the limb disposed within the splint 102 and resting upon the foam mattress 104. When the valve 108 is opened, the excess air pressure in portion 102 then transferred to the second portion 104.

As portion 1 deflates, the filling material of the splint 102 then becomes more compact and rigid. The splint 102 may accurately encapsulates the contours of the limb and hardens, providing the security of a splint encasing the limb without creating pressure points. Similarly, as the splint 102 deflates, the foam portion 104 inflates.

When using memory foam, the portion 104 can inflate to a known position. FIG. 2B illustrates the front view showing how the second portion 104 includes a notch in the middle, allowing the limb (in the splint) to rest within the notch.

Also visible, in a comparison of FIG. 1 to FIG. 2a and FIG. 1a to FIG. 2b, the first portion 102 is then smaller as it is deflated and the second portion is larger as it is inflated.

FIG. 3 illustrates another embodiment of a splint 120. This exemplary embodiment is in the shape of a boot, usable when the limb in question is a leg or ankle. The splint 120 is illustrates with an air tube 122 and valve 124 for connection with a second portion and sequent release or change in air pressure. In this exemplary embodiment, the splint can encapsulate the person's whole ankle and foot for improved immobilization.

FIG. 4 illustrates one embodiment of a foam pillow in a compressed state. The foam pillow may include memory foam and be encapsulated in an air tight container. In this embodiment, the memory foam, when expanded may exert external pressure on the casing of the second portion to help draw the air from the first portion.

Figure 5:
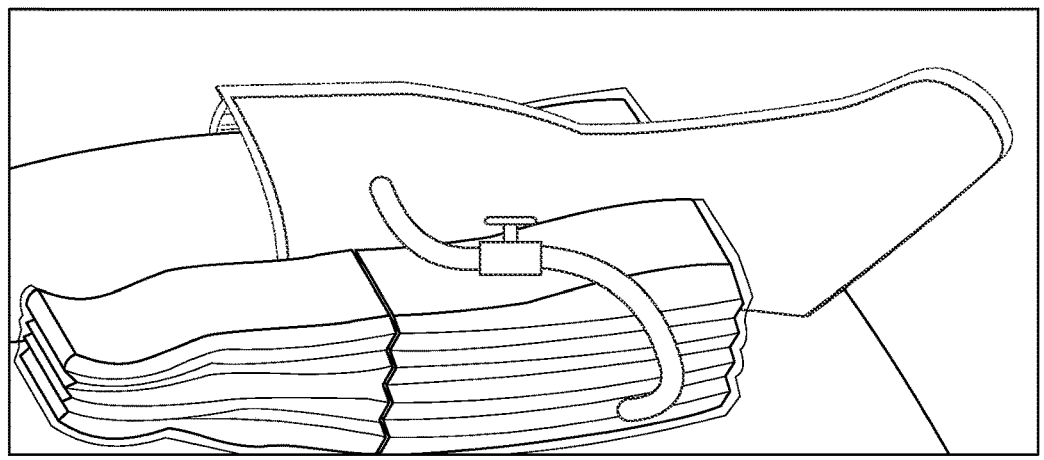
FIG. 5 illustrates a representation of another embodiment of the second element in an inflated state.

FIG. 5 illustrates the placement of a limb on the foam pillow 130 in the compressed state. In this example where the limb is a leg, the calf portion is disposed on the compressed pillow. Unlike previous techniques, the foam pillow may be readily slid under the leg without having to move the leg as much as compared with an inflated pillow.

In the illustration of FIG. 5, the limb is encased in the splint/immobilization portion, where the splint/immobilization portion is inflated and the pillow portion is deflated.

Figure 6:
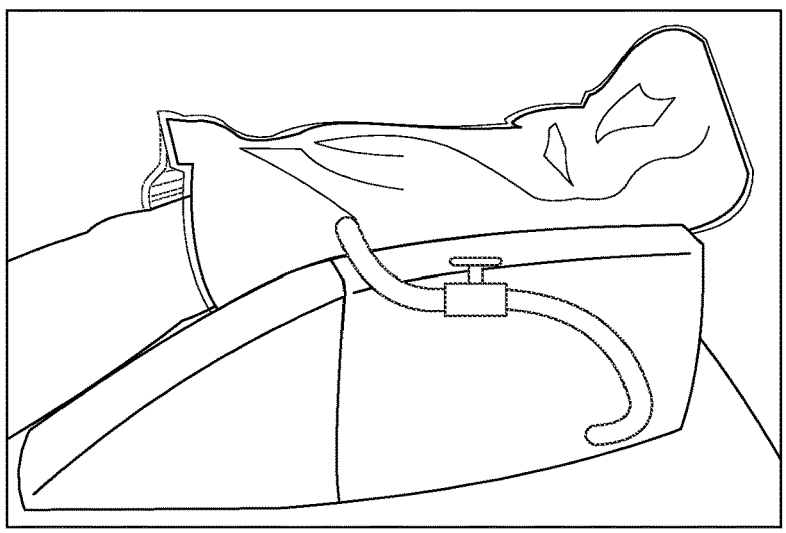
FIG. 6 illustrates a representation of combination of the first element and the second element.

When the air flow valve is released, the splint then deflates and the pillow inflates. FIG. 6 illustrates the portions when the airflow has been completed. In this example, the limb is disposed within the splint and the limb/splint rests comfortably within the contour of the pillow. In one embodiment, the air valve may then be closed to insure proper re-alignment of air pressure and inflation/deflation status of the first and second portions.

Figure 7:
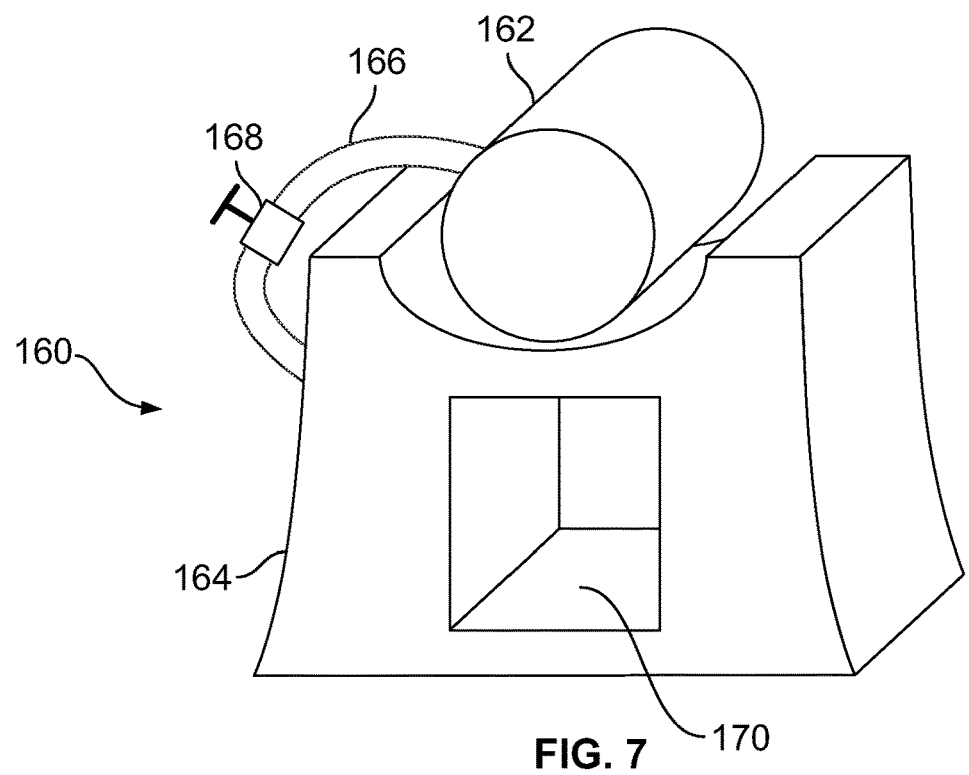
FIG. 7 illustrates a front view of another embodiment of the first element and second element in combination.

FIG. 7 illustrates another embodiment 160 having the first portion 162, the second portion 164, air tube 166 and valve 168. In this embodiment, the second portion 164 includes a cut-out 170 allowing for access to the underside of the splint. For example, the slot 170 can allow for the inclusion of an ultrasound probe, such as for insertion of an ultrasound guided popliteal nerve block. It is recognized that other types of uses are envisioned herewith and are within the scope of this invention.

Figure 8:
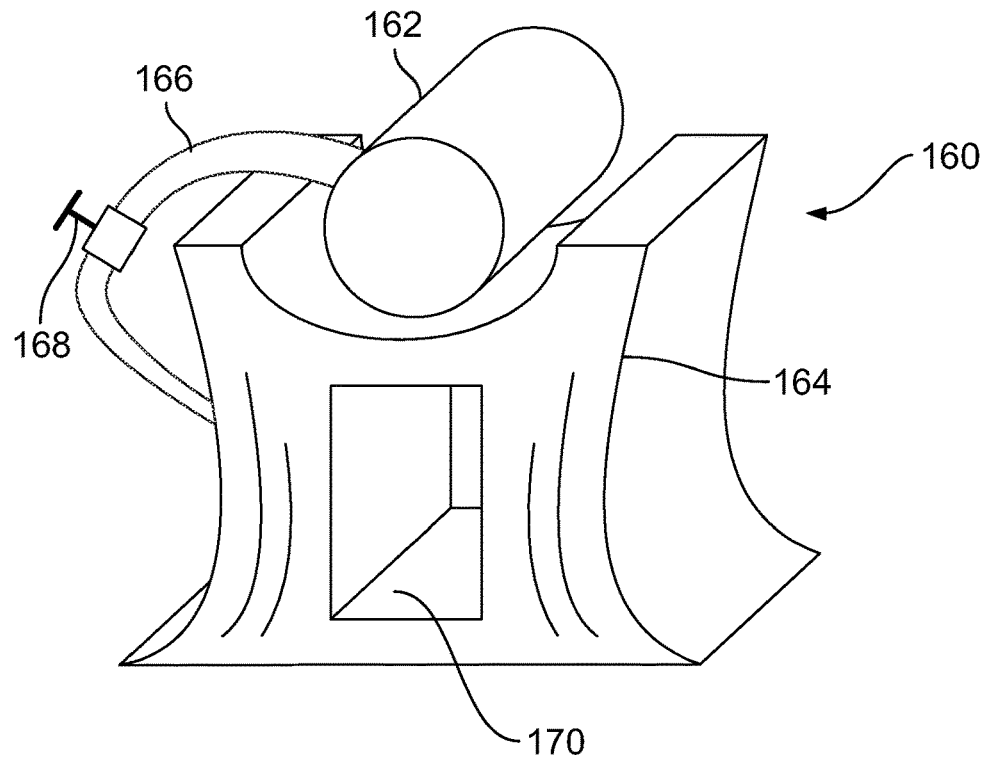
FIG. 8 illustrates a front view of the embodiment of FIG. 7 having the both portions at ambient pressure.

FIG. 8 illustrates the adjustment of the air pressure to an ambient pressure, wherein the first portion 162 is then smaller in diameter and then second portion is fully inflated, similar to operations described above. In one embodiment, the air valve may be adjusted to offset pressure between the portions, including allowing the pillow to slightly deflate to give a better cushion, or relieving some pressure on the splint first portion. Similarly, if release of pressure in one portion does not want to adjust pressure in the other portion, the air pressure on the designated portion may be adjusted by directly releasing air pressure or air volume for that portion, e.g. removing the air tube from the valve to release air pressure/air volume.

The top bag is now formed and held around the lower leg in the desired position of the lower leg (or whatever limb or body part), and the pressure inside the bag is that or ambient. When the open-to-close valve, which connects the upper and lower bag is switched to the open position, the foam inside the lower pillow resumes its original form by expanding, which creates negative pressure (suction) which in turn deflates the upper bead-filled bag which will now assume the desired hard shape around the limb or other body part (neck, knee, etc., for example), similar to the "bean bag" without exerting any pressure upon the limb and without causing any potential pressure points or impeding its blood supply.

The inflation/deflation serves a dual purpose. Because the lower pillow inflates and assumes its original pre-compressed form, which can be used (amongst other things) to elevate the limb, which not only provides comfort, but also has numerous other medical benefits (i.e. reduction of swelling, etc.). The upper bead-filled bag now deflates (due to the suction generated by the bottom pillow returning to its original form) and splints the limb into position.

When the splint (bead-filled bag) or the support (pillow) is no longer needed, the valves are all opened and ambient pressure will return to the bead-filled bag both will retain their original form. Applying external positive pressure (standing on it or compressing it somehow for example) or negative pressure (suction) to it, will again compress the inner foam of the lower pillow for re-use later or for easy space-saving storage.

All upper and lower parts/pillows/bags can, after inflation or deflation be easily disconnected from each other whilst retaining it's state of inflation (either inflated or deflated) to be used elsewhere. For example, a total leg splint can be used to splint the knee after total knee replacement surgery, to allow the patient to ambulate without the fear of falling because of quadriceps muscle weakness. The deflated bead-filled bag, now hard, acts as a lightweight knee splint for safe and easy ambulation. If splinting is not required the lower pillow can be used on its own. The upper pillow can be used in a semi-deflated state to keep the limb in position, or totally inflated for comfort.

Potential applications, by way of example and not a limiting or exhaustive list include: 1. Lower leg elevator with tibia/fibula/ankle splint; 2. Total leg elevator with knee/tibia/fibula/femur/ankle splint; 3. Leg adduction pillow with both or one leg splint; 4. Total body positioning splint on inflatable stretcher; 5. Lower arm elevation with radius/ulna/wrist/elbow splint. 6. Upper arm humerus, shoulder splint; and 7. Pillows for comfortable arm positioning (in an aircraft seat for example) with neck lower jaw splint for comfortable sleeping and airway protection in the sitting position or after neck trauma.

To put it differently, the current invention incorporates a beanbag that is shaped to accommodate a limb or other body part or entire body (typically as a shaped tube that fits around a limb), and a deflation device. The difference, however, is that, although the shaped beanbag can be deflated by a regular AC or DC power or mechanical suction device (hand pump for example), the suction device (deflation device) of this invention is typically a pillow or cushion or splint with another useful function that is, in its storage state, compressed by either suctioning the air out of its container or using gravity to compress it by, for example, standing on it or otherwise compressing it. This device is connected to the bead-filled bag and upon releasing the negative pressure created to the beanbag it inflates itself and deflates (applies suction to) the bead-filled bag. The inflated device now serves as another useful device such as a pillow or cushion or elevation device for an injured leg, or part of the positioning device, etc. The beanbag then molds itself around the limb or body part or total body while the deflation device adopts some other useful purpose.

Further embodiments may include a neck brace for emergency splinting: Emergency neck bracing is standard of care for any patient who sustained any form of trauma, being that motor vehicle injuries, sport injures, etc. The neck brace is routinely placed to prevent further injuries, and to place a brace should not allow any manipulation of the potentially injured neck and spinal cord. A hard pre-formed standard neck brace is thus potentially dangerous, as the patient has to be lifted or the neck flexed to place such a device in place. A flat cross-shaped un-deflated (or partially inflated) soft beanbag is slipped in behind the head, neck and back of a patient and the arms of the cross are shaped around the neck of the patient. The bag is deflated by opening the connection between the deflation device, which contains negative pressure. The neck brace deflates and mold itself around the head and neck of the patient and in doing so splints the neck without exerting any pressure to compromise the airway or the cerebral vasculature (blood flow) and avoiding pressure points to develop. It can also maintain the airway of the patient. While the splint forms and molds itself, the deflation device inflates and assumes the form of a head cushion, lumbar support, or other useful device—even a stretcher or anti-shock inflation device. This way no electrical suction apparatus is required and the deflation device serves a dual function, and can be used in the field or austere environments where electricity is not readily available. Because the deflation device before use contains negative pressure, it is small, lightweight and easy to store and transport. The beanbag portion is lightweight and soft and small and is also easy to transport and store and can even used for another function at this stage, such as a soft sleeping or resting pillow.

Another embodiment is a neck brace for airline traveling: Numerous devices have been tried to stabilize the head and neck of an airline passenger while keeping their airways open when the passenger tries to sleep in the upright position on long flights. These have universally been met with failure because most, if not all, are ineffective to stabilize the head and neck and all do not protect the airway (prevent snoring and sleep apnea) and most, if not all, are bulky and clumsy to carry on board. This invention would be easy to carry on boards and is small and light when not in use. The neck brace is lightweight and can be used as a pillow before deflating it, i.e. before the passenger elects to sleep. It basically works exactly like 1. above, except that the useful purpose of the deflation device could be in the shape of pillows formed to position the arms in a comfortable position on the armrests of the seat, and prevent pressure on sensitive tissue like the ulnar nerves and radial nerves, a common problem caused by seats in airplanes.

Another embodiment is an emergency splinting of ankle fractures: With the population getting heavier, ankle fractures are very common and most, if not all, end up being surgically fixated. As an emergency measure before surgery, in the field for example, the ankle has to be fixated without increasing pressure on the traumatized tissue and thus compromising blood flow by creating a tight compartment. This requirement makes standard bandaging and casting dangerous and problematic. Another essential part of the emergency treatment is to elevate the ankle to reduce or prevent swelling. This invention proposes a beanbag that is shaped to form a tube that fits around the lower leg, ankle and foot that, when deflated, exerts no pressure on the ankle but firmly splints it such the fracture segments cannot move and further injury is avoided. The deflation device can be in the form of a leg elevator such that the leg can be ideally positioned for ultrasound-guided popliteal nerve blocks.

Another embodiment is an emergency arm splint: The principles for this application are similar to that of the splint for ankle. The same consideration for nerve block applies.

Another embodiment is an emergency splint for femur fracture: The principles for this application are similar to that of the splint for ankle fractures. The same consideration for nerve block applies.

Another embodiment is for positioning for nerve blocks: This is a wide-open field and nothing is currently available. The same principles as outlined above can be used for optimal positioning for labor epidurals and a host of other peripheral nerve blocks, where the deflation device becomes part of the positioning device. Again, transport and storage would be optimized because the deflation device is suctioned flat prior to its use.

Another embodiment is for positioning on operating room tables: There is a huge demand to replace the so-called "axillary roll" for patients in the lateral decubitus position. Both the beanbag and deflation apparatus are ideally suited to replace these.

Another embodiment is for splinting of knees after total knee arthroplasty: There is a big fall risk with early ambulation of these patients especially after continuous femoral nerve blocks that temporarily paralyzes the quadriceps muscles, and a beanbag-deflation device is ideally suited here as well.

There are numerous other applications, for example hand splints that are not included in this brief outline. The deflation device can even be used as compression device around the lower extremities to restore blood volume in case of hypovolemic shock.

In addition to the above uses described above, a further embodiment may include an air flow regulator device connected between the first portion and the second portion. While one embodiment relies on ambient pressure to inflate the second portion and deflate the first portion, in some scenarios that may not be preferred. For example, if a person's limb is very large, the weight of the limb may prevent the second portion from inflating and therefore prevent the first portion from deflating. Thus, one embodiment may include an air flow regulator disposed between the two portions for controlling the air flow, such as extracting air from the first portion and/or inserting air into the second portion.

Figures presented herein are conceptual illustrations allowing for an explanation of the present invention. Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, Applicant does not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments so fully reveals the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein.

What is claimed is:

1. An immobilization device comprising:
   an inflated first portion capable of being secured around a limb;
   a deflated second portion engaged with the first portion, the second portion including foam material encapsulated in an air tight membrane; and
   an air tube connecting the first portion and the second portion, the air tube having a valve disposed between the first portion and the second portion;
   wherein the limb may be secured within the inflated first portion and upon engagement of the valve, the foam material of the second portion expands within the air tight membrane causing the first portion to deflate to further immobilize the limb, the expanding of the foam material of the second portion elevating the limb.

2. The immobilization device of claim 1, wherein the first portion is a splint such that the deflation of the first portion generates rigidity within the splint.

3. The immobilization device of claim 1, wherein the first portion may be in an original deflated position prior to being secured to the limb, the first portion including an air inlet valve for being inflated after being secured around the limb.

4. The immobilization device of claim 1, wherein the first portion includes a plurality of beads embedded therein, such that when the first portion is deflated, the beads form a securing shape around the limb.

5. The immobilization device of claim 1, wherein the foam material of the second portion comprises memory foam such that when the second portion is inflated, the memory foam returns to a predetermined position.

6. The immobilization device of claim 1 further comprising:
   an air inlet valve for inflating at least one of the first portion and the second portion.

7. The immobilization device of claim 1, wherein the first portion is sized to secure a leg.

8. The immobilization device of claim 1, wherein the first portion is sized to secure an upper body portion.

9. The immobilization device of claim 1, wherein the inflation of the first portion may be performed using an air pump device.

10. An immobilization method comprising:
    securing a limb in a first portion, the first portion being inflated;
    positioning the limb, secured in the first portion, upon a second portion, the second portion being deflated and including foam material encapsulated in an air tight membrane, where the first portion is connected to the second portion via an air tube; and
    opening an air valve disposed between the first portion and the second portion such that the foam material of the second portion expands within the air tight membrane transferring the air from the first portion into the second portion where the first portion deflates to further immobilize the limb and the second portion inflates to elevate the limb.

11. The method of claim 10 wherein the first portion is a splint such that the deflation of the first portion generates rigidity within the splint.

12. The method of claim 10 wherein the second portion is a pillow such that inflation of the second portion elevates the limb.

13. The method of claim 10 further comprising:
    securing the first portion to the limb while the first portion is in a deflated position; and
    inflating the first portion using an air inlet valve.

14. The method of claim 10, wherein the first portion includes a plurality of beads embedded therein, such that when the first portion is deflated, the beads form a securing shape around the limb.

15. The method of claim 10, wherein the foam material of the second portion includes memory form such that when the second portion is inflated, the memory foam returns to a predetermined position.

16. The method of claim 10, wherein the limb is a leg.

17. An immobilization device comprising:
    an inflated first portion capable of being secured around a limb, wherein the first portion is a splint such that the deflation of the first portion generates rigidity within the splint;
    a deflated second portion engaged with the first portion wherein the second portion includes a pillow encapsulated in an air tight membrane; and
    an air tube connecting the first portion and the second portion, the air tube having a valve disposed between the first portion and the second portion;
    wherein the limb may be secured within the inflated first portion and upon engagement of the valve, the pillow of the second portion expands within the air tight membrane causing the first portion to deflate to further immobilize the limb and such that inflation of the pillow of the second portion elevates the limb.

18. The immobilization device of claim 17, wherein the first portion is sized to secure a leg.

19. The immobilization device of claim 17, wherein the first portion is sized to secure an upper body portion.

20. The immobilization device of claim 17 further comprising a plurality of beads embedded within the first portion.

* * * * *